United States Patent
Gyory

(10) Patent No.: US 8,224,435 B2
(45) Date of Patent: Jul. 17, 2012

(54) ELECTROTRANSPORT DEVICE HAVING A RESERVOIR HOUSING HAVING A FLEXIBLE CONDUCTIVE ELEMENT

(75) Inventor: J. Richard Gyory, Sudbury, MA (US)

(73) Assignee: Alza Corporation, Vacaville, CA (US)

( * ) Notice: Subject to any disclaimer, the term of this patent is extended or adjusted under 35 U.S.C. 154(b) by 1279 days.

(21) Appl. No.: 10/814,705

(22) Filed: Mar. 30, 2004

(65) Prior Publication Data

US 2005/0004506 A1   Jan. 6, 2005

Related U.S. Application Data

(60) Provisional application No. 60/459,539, filed on Mar. 31, 2003.

(51) Int. Cl.
*A61N 1/30* (2006.01)
(52) U.S. Cl. .......................................................... 604/20
(58) Field of Classification Search .................. 607/152; 604/20, 501, 503
See application file for complete search history.

(56) References Cited

U.S. PATENT DOCUMENTS

| | | | |
|---|---|---|---|
| 4,141,359 A * | 2/1979 | Jacobsen et al. | 604/20 |
| 4,747,819 A * | 5/1988 | Phipps et al. | 604/20 |
| 4,911,688 A * | 3/1990 | Jones | 604/20 |
| 5,006,108 A | 4/1991 | La Prade | |
| 5,047,007 A | 9/1991 | McNichols et al. | |
| 5,158,537 A | 10/1992 | Haak et al. | |
| 5,224,927 A * | 7/1993 | Tapper | 604/20 |
| 5,224,928 A | 7/1993 | Sibalis et al. | |
| 5,246,418 A | 9/1993 | Haynes et al. | |
| 5,254,081 A | 10/1993 | Maurer et al. | |
| 5,288,289 A | 2/1994 | Haak et al. | |
| 5,310,404 A | 5/1994 | Gyory et al. | |
| 5,320,598 A | 6/1994 | Haak et al. | |
| 5,830,175 A * | 11/1998 | Flower | 604/20 |
| 5,857,994 A * | 1/1999 | Flower | 604/20 |
| 6,195,582 B1 | 2/2001 | Scott | |
| 6,295,469 B1 * | 9/2001 | Linkwitz et al. | 604/20 |
| 6,629,968 B1 * | 10/2003 | Jain et al. | 604/501 |
| 6,653,014 B2 * | 11/2003 | Anderson et al. | 429/122 |
| 6,915,159 B1 * | 7/2005 | Kuribayashi et al. | 604/20 |

FOREIGN PATENT DOCUMENTS

WO   96/09851 A1   4/1996
WO   96/17650 A1   6/1996

OTHER PUBLICATIONS

International Search Report dated Aug. 19, 2004 for corresponding Appln. No. PCT/US04/009831.

* cited by examiner

*Primary Examiner* — Kevin C Sirmons
*Assistant Examiner* — Andrew Gilbert
(74) *Attorney, Agent, or Firm* — Michael J. Atkins

(57) ABSTRACT

This invention relates to an electrotransport device, which incorporates a flexible conductive element within the reservoir housing of the device, which permits electrical communication from within the housing to outside of the housing without the use of opening, which require various methods of sealing the opening against leaks and moisture.

6 Claims, 2 Drawing Sheets ly ELECTROTRANSPORT DEVICE HAVING A
RESERVOIR HOUSING HAVING A FLEXIBLE
CONDUCTIVE ELEMENT

TECHNICAL FIELD

This application claims the benefit of U.S. Provisional Application No. 60/459,539, filed Mar. 31, 2003.

The present invention relates to a transdermal therapeutic agent delivery and sampling device having a reservoir housing having a flexible electrically conductive element integrally molded within the generally non-conductive housing. This flexible/bendable electrically conductive element allows an electrical connection to be made across the reservoir housing without physically passing cables or wires through an opening in the housing. This flexible electrically conductive element permits an electrical connection between the controller and other electrical components, located outside of the reservoir housing, and the electrode which is mounted inside of or is part of the reservoir housing.

BACKGROUND ART

The term "electrotransport" refers generally to the delivery or extraction of a therapeutic agent (charged, uncharged, or mixtures thereof) through a body surface (such as skin, mucous membrane, or nails) wherein the delivery or extraction is at least partially induced or aided by the application of an electric potential. The electrotransport process has been found to be useful in the transdermal administration of many drugs including lidocaine, hydrocortisone, fluoride, penicillin, and dexamethasone. A common use of electrotransport is in diagnosing cystic fibrosis by delivering pilocarpine iontophoretically. The pilocarpine stimulates production of sweat. The sweat is then collected and analyzed for its chloride content to detect the presence of the disease.

Electrotransport devices generally employ two electrodes, positioned in intimate contact with some portion of the body, typically the skin. A first electrode, called the active or donor electrode, is used to deliver the therapeutic agent into the body. The second electrode, called the counter or return electrode, closes an electrical circuit with the first electrode through the body. A source of electrical energy, such as a battery, supplies electric current to the body through the electrodes. For example, if the therapeutic agent to be delivered into the body is a positively charged cation, the anode is the active electrode and the cathode is the counter electrode required to complete the circuit. If the therapeutic agent to be delivered is a negatively charged anion, the cathode is the donor electrode and the anode is the counter electrode.

A widely used electrotransport process, electromigration (also called iontophoresis), involves the electrically induced transport of charged ions (e.g., drug ions) through a body surface. Another type of electrotransport, called electroosmosis, involves the trans-body surface (e.g., transdermal) flow of a liquid under the influence of the applied electric field. Still another type of electrotransport process, called electroporation, involves forming transiently existing pores in a biological membrane by applying high voltage pulses. In any given electrotransport system, one or more of these processes may occur to some extent simultaneously.

Most transdermal electrotransport devices have an anodic and a cathodic electrode assembly. Each electrode assembly is comprised of an electrically conductive electrode in ion-transmitting relation with an ionically conductive reservoir which is placed in contact with the patient's skin during use. A hydrogel reservoir such as described in Webster, U.S. Pat. No. 4,383,529 is the preferred form of reservoir since hydrated gels are easier to handle and manufacture than liquid-filled reservoirs. Water is by far the preferred liquid solvent for use in such reservoirs. This is in part because many drug salts are water-soluble and in part because water has excellent biocompatability, making prolonged contact between the reservoir and the skin acceptable from an irritation standpoint.

The term "agent" is intended to have its broadest interpretation and is used to include any therapeutic agent or drug, as well as any body analyte, such as glucose. The terms "drug" and "therapeutic agent" are used interchangeably to refer to any therapeutically active substance that is delivered to a living organism to produce a desired, usually beneficial, effect. This includes therapeutic agents in all the major therapeutic areas including, but not limited to: anti-infectives such as antibiotics and antiviral agents; analgesics, including fentanyl, sufentanil, remifentanil, buprenorphine and analgesic combinations; anesthetics; anorexics; antiarthritics; antiasthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers.

The term "flexible" is intended to have its standard meaning which means that a material has the property of being able to be bent without breaking.

Of particular interest in transdermal delivery is the delivery of analgesic drugs for the management of moderate to severe pain. Control of the rate and duration of drug delivery is particularly important for transdermal delivery of analgesic drugs to avoid the potential risk of overdose and the discomfort of an insufficient dosage. One class of analgesics that has found application in a transdermal delivery route is the synthetic opiates, a group of 4-aniline piperidines. The synthetic opiates, e.g., fentanyl and certain of its derivatives such as sufentanil, are particularly well suited for transdermal administration. These synthetic opiates are characterized by their rapid onset of analgesia, high potency, and short duration of action. They are estimated to be 80 and 800 times, respectively, more potent than morphine. These drugs are weak bases, i.e., amines, whose major fraction is cationic in acidic media.

Electrotransport devices use at least two electrodes that are in electrical contact with some portion of the skin, nails, mucous membrane, or other surface of the body. One electrode, commonly called the "donor" electrode, is the electrode from which the therapeutic agent is delivered into the body. The other electrode, typically termed the "counter" electrode, serves to close the electrical circuit through the body. For example, if the therapeutic agent to be delivered is a positively charged cation, then the anode is the donor electrode, while the cathode is the counter electrode, which serves to complete the circuit. Alternatively, if a therapeutic agent is a negatively charged anion, the cathode is the donor electrode and the anode is the counter electrode. Additionally, both the anode and cathode may be considered donor electrodes if both anionic and cationic therapeutic agent ions, or if uncharged dissolved therapeutic agent, are to be delivered.

Furthermore, electrotransport delivery systems generally require at least one reservoir or source of the therapeutic agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more therapeutic agents or drugs. Electrotransport devices are powered by an electrical power source such as one or more batteries. Typically, at any one time, one pole of the power source is electrically connected to the donor electrode, while the opposite pole is electrically connected to the counter electrode. Since it has been shown that the rate of electrotransport drug delivery is approximately proportional to the electric current applied by the device, many electrotransport devices typically have an electrical controller that controls the voltage and/or current applied through the electrodes, thereby regulating the rate of drug delivery. These control circuits use a variety of electrical components to control the amplitude, polarity, timing, waveform shape, etc. of the electric current and/or voltage supplied by the power source. See, for example, McNichols et al., U.S. Pat. No. 5,047,007.

To date, commercial transdermal electrotransport drug delivery devices (e.g., the Phoresor, sold by Iomed, Inc. of Salt Lake City, Utah; the Dupel Iontophoresis System sold by Empi, Inc. of St. Paul, Minn.; and the Webster Sweat Inducer, model 3600, sold by Wescor, Inc. of Logan, Utah) have generally utilized a desk-top electrical power supply unit and a pair of skin contacting electrodes. The donor electrode assembly contains a drug solution while the counter electrode assembly contains a solution of a biocompatible electrolyte salt. The power supply unit has electrical controls for adjusting the amount of electrical current applied through the electrodes. The "satellite" electrodes are connected to the electrical power supply unit by long (e.g., 1-2 meters) electrically conductive wires or cables. The wire connections are subject to disconnection and limit the patient's movement and mobility. Wires between electrodes and controls may also be annoying or uncomfortable to the patient. Other examples of desk-top electrical power supply units which use "satellite" electrode assemblies are disclosed in Jacobsen et al., U.S. Pat. No. 4,141,359 (see FIGS. 3 and 4); LaPrade, U.S. Pat. No. 5,006,108 (see FIG. 9); and Maurer et al., U.S. Pat. No. 5,254,081.

More recently, electrotransport delivery devices have become much smaller, particularly with the development of miniaturized integrated circuits and more powerful light weight batteries (e.g., lithium batteries). The advent of inexpensive miniaturized electronic circuitry and compact, high-energy batteries has meant that the entire device can be made small enough to be unobtrusively worn on the skin of the patient, under clothing. This allows the patient to remain fully ambulatory and able to perform all normal activities, even during periods when the electrotransport device is actively delivering drug. Such small self-contained electrotransport delivery devices are disclosed for example in Tapper, U.S. Pat. No. 5,224,927; Sibalis et al., U.S. Pat. No. 5,224,928; and Haynes et al., U.S. Pat. No. 5,246,418.

Reference is now made to FIG. 1 which depicts an exploded view of an exemplary electrotransport device 10 having an activation switch in the form of a push button switch 12 and a display in the form of a light emitting diode (LED) 14. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 may have lateral wings 15, which assist in holding device 10 on a patient's skin. Upper housing 16, when molded with the lateral wings, is generally composed of rubber or other elastomeric material, such as an ethylene vinyl acetate (EVA), silicone, polyolefinic elastomers (Engage®), or similar material. Upper housing 16, if not molded with the lateral wings, could be made of a more rigid material such as styrene, polypropylene, polyethylene or other similar material. Lower housing 20 is typically composed of a plastic or elastomeric sheet material (such as polyethylene terephthalate glycol (PETG) or polyethylene) which can be easily molded or thermoformed to form depressions for the reservoirs and the electrodes. The sheet material can easily be cut to form openings 23 and 23' therein. Alternately the lateral wings can be an integral part of the lower housing. In this case, the lower housing may be molded using an elastomeric material or thermoformed using a flexible material. Printed circuit board assembly 18 comprises an integrated circuit 19 coupled to discrete electrical components 40 and battery 32. Circuit board assembly 18 is attached to housing 16 by posts (not shown in FIG. 1) passing through openings 13$a$ and 13$b$, the ends of the posts being heated and/or melted in order to heat stake the circuit board assembly 18 to upper housing 16. Alternate forms of assembly include the use of snap fit components, ultrasonic welding, screws, rivets or friction fit. Lower housing 20 is attached to the upper housing 16 by means of adhesive 30, the upper surface 34 of adhesive 30 being adhered to both lower housing 20 and upper housing 16 including the bottom surfaces of wings 15, if present.

On the underside of circuit board assembly 18 is battery 32, which serves as the power source for the device and which may be a button cell battery, such as a lithium cell. The circuit outputs of the circuit board assembly 18 make electrical contact with the electrodes 24 and 22 through openings 23, 23' in the depressions 25, 25' formed in lower housing 20 by means of electrically conductive adhesive 42, 42'. Electrodes 22 and 24, in turn, are in direct electrical and/or mechanical contact with the top sides 44', 44 of drug reservoir 26 and the non-drug containing electrolyte reservoir 28. The bottom sides 46', 46 of reservoirs 26, 28 contact the patient's skin through the openings 29', 29 in adhesive 30. Upon depression of push button switch 12, the electronic circuitry on circuit board assembly 18 delivers a predetermined direct current (DC) to the electrodes/reservoirs 22, 26 and 24, 28 for a delivery interval of predetermined length.

Electrotransport delivery devices are prepared, shipped, and stored (or stored, shipped, and stored), prescribed and then used. As a result, the devices must have components that have extended shelf lives that, in some instances, must comply with regulatory requirements. For instance, the U.S. Food and Drug Administration has shelf life requirements of from six to eighteen months or more for some materials. One complicating factor in achieving an extended shelf life is the stability of the system components when exposed to elevated temperatures. In order to achieve satisfactory dimensional stability of the elastomeric system components, the molding conditions as well as secondary manufacturing operations must be carefully optimized, requiring narrow ranges of process parameters, to avoid warpage, deformation and/or unacceptable dimensional changes. If the device housing should encounter elevated temperatures (i.e. over 40° C.) during storage or shipping these same undesirable deformations or dimensional changes may occur.

Further, electrotransport delivery devices typically contain electronic components (e.g., integrated circuits, resistors, diodes capacitors, inductors, etc.), conductive circuit traces, and electrical as well as physical connections therebetween which can corrode or otherwise be degraded by water or water vapor. Devices such as device 10 shown in FIG. 1 have hydratable or hydrated reservoirs 26, 28. Thus, humidity or moisture from the hydrated reservoirs can permeate or leak through the reservoir housing during manufacturing and storage. The moisture can thus cause corrosion of the electronic and/or mechanical components within the device, thereby reducing the shelf life of the device. One source of permeation or leaks is around the electrodes or around the electrical leads or contacts, which must supply electric current and voltage from the battery into the relatively wet environment inside of the reservoir housing.

In order to apply voltage from a power source to the donor reservoir, there must be some method or device used to place the power source in electrical communication with the donor reservoir.

One method is to mold, punch, drill, or in some other manner fabricate an opening in the housing used to contain the drug reservoir. An electrode is then placed or adhered on the inside of the housing, thus making the electrode accessible through the opening. The drug reservoir is then placed within the reservoir cavity so that it is in electrical contact with the electrode. Thereafter, electrical contact can be made with the drug reservoir via that portion of the electrode that is exposed by the opening in the reservoir housing.

There are several critical points in the implementation of this method. All of which involve sealing the opening in the reservoir housing. Because the drug reservoirs are often largely water, there is tendency for this liquid, moisture and/or humidity to escape from the housing and corrode the electronic and/or mechanical components if there is not proper sealing between the electrode and the drug reservoir housing. Because these devices are shipped and stored in sealed pouches, any water or moisture escaping from the reservoir will be trapped in the interior of the device and expose the controller circuitry and other electrical components to the water. Water, particularly water containing electrolyte salts which are typically found in the drug reservoir, can be very corrosive and quite damaging to the device.

One solution has been to develop dry or non-hydrated electrodes. See for example U.S. Pat. Nos. 5,158,537; 5,288,289; 5,310,404; and 5,320,598. Because the electrode only needs to be hydrated during actual use by the patient during drug delivery, the device can be manufactured and stored with the reservoir in a dry or non-hydrated state. Then a hydrating liquid, with or without the agent dissolved therein, is added to the reservoir just prior to use. But there are a number of design considerations that must be taken into account when this approach is used and it introduces its own set of challenges. Problems arise regarding dehydrating and rehydrating without damaging the drug reservoir and assuring the adequate and timely resolubilization of the active agent upon rehydration.

Other approaches have been to make the device resistant to moisture and corrosion. One step that has been taken to combat the corrosion problem has included gold plating the electrical and/or mechanical connectors (such as contacts or contact tabs) and circuit board traces. Such solutions are inherently expensive and add additional steps to the manufacturing process.

Other tactics used to deal with the moisture and corrosion problem has been to seal the electronics in a conformal coating, to package the hydrogel separately and to include desiccant in the pouch containing the device.

Use of conformal coatings requires an additional processing step which increases costs and production time. Packaging the drug reservoir gels separately also increases costs and production time and also includes additional steps for the patient who must then assemble the device prior to use. Desiccants in the device pouch also require additional components and also tend to dehydrate the gel reservoirs in the pouches which results in decreased efficiency when used by the patient.

DESCRIPTION OF THE INVENTION

The present invention provides an electrotransport reservoir housing having a flexible conductive element integrally molded within the insulated housing so that a first portion of the element is within the housing and the second portion is outside of the housing. The incorporation of this flexible conductive element as part of the reservoir housing enables placing the drug reservoir and electrode, which are inside of the reservoir housing, in electrical communication with a power source outside of the reservoir, without the need for an opening to be formed in the reservoir housing after it has been formed. Because the molding process is performed at high heat and pressure, there is a very tight, liquid and moisture impermeable bond that is created between the material forming the reservoir housing and the conductive element. This results in a reservoir housing that is essentially a single integral component that does not require the fabrication of openings or other passages through the housing which would require subsequent sealing. By having a conductive element molded into and through the housing during manufacture, it eliminates problems of water and/or moisture from the drug reservoir contained within the interior of the reservoir housing leaking through or otherwise coming in contact with the electrical and/or mechanical components outside of the reservoir housing.

BRIEF DESCRIPTION OF THE DRAWINGS

A better understanding of the present invention as well as other objects and advantages thereof will become apparent upon consideration of the following detailed description especially when taken with the accompanying drawings, wherein like numerals designate like parts throughout, and wherein.

MODES FOR CARRYING OUT THE INVENTION

Figure 1:
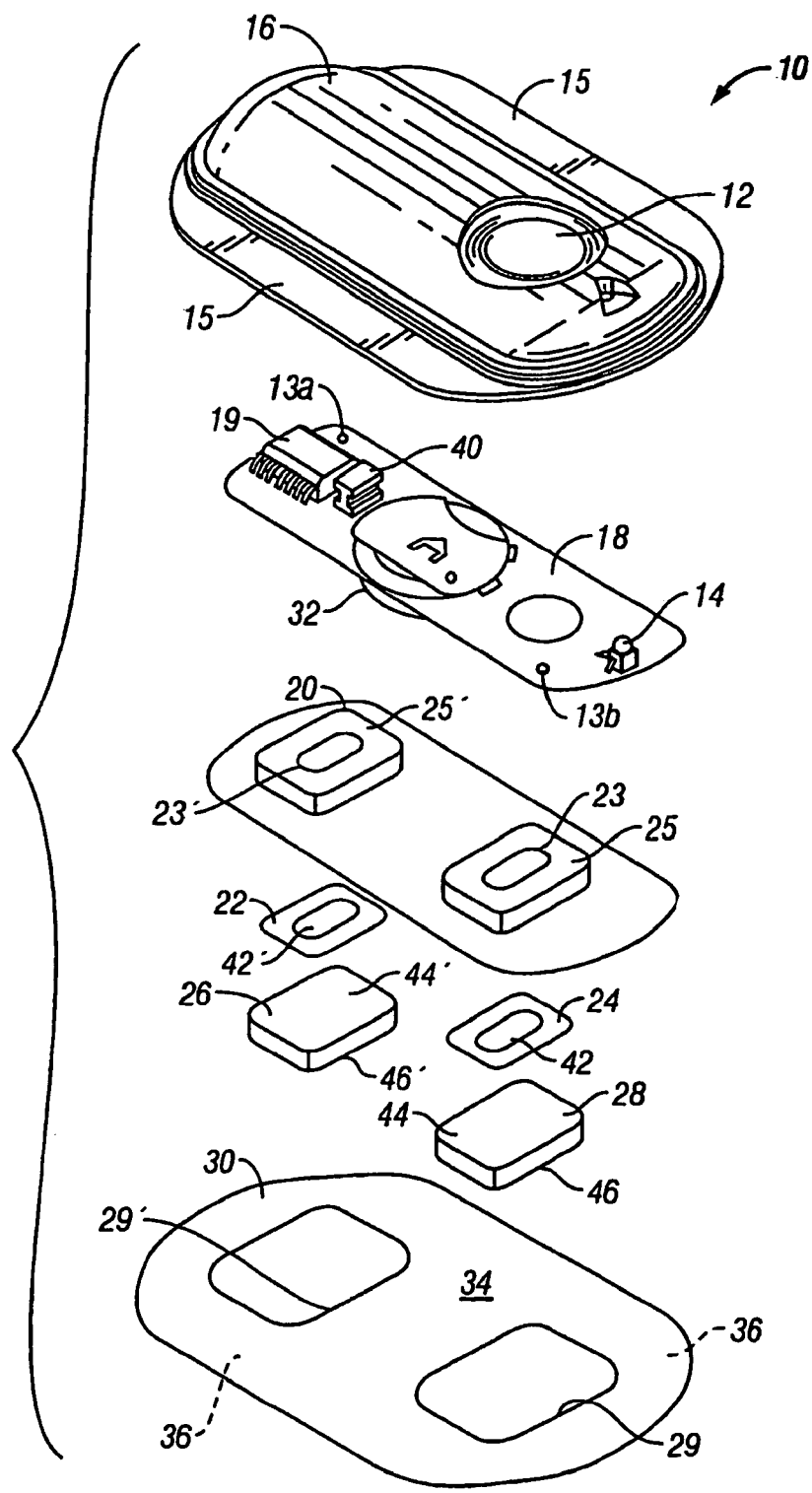
FIG. 1 is an exploded view of a prior art electrotransport device.
Figure 2:
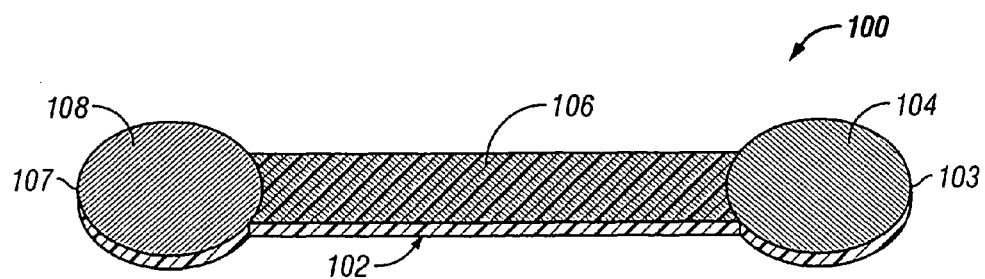
FIG. 2 is a perspective view of the flexible conductive element.

The following discussion will be made with reference to FIGS. 2-4. The present invention calls for the use of a Flexible Conductor 100 which is comprised of Electrode End 103 and Contact End 107 and a Connecting Portion 102 which runs between the two ends. A conductive coating is applied to the surfaces of Electrode End 103 and Contact End 107 and the Connecting Portion 102. Each of the three regions may be coated with a different material because the coating for each region serves a different purpose and has different requirements.

Electrode End 103, which will be located within the reservoir housing, will serve as part of the electrode assembly and will be coated with Electrode Coating 104 which is a conductive material that fulfills the electrochemistry needs of a conductive surface located within the reservoir housing. Such material would typically be a Ag/AgCl ink. Alternatively, a separate Ag/AgCl electrode (not shown) may be positioned within the reservoir housing so as to be in direct contact with Electrode End 103 and the reservoir gel or reservoir matrix. In this case, a special coating on Electrode End 103 may not be required and any conductive coating that is suitable for use in the moisture rich environment of the reservoir housing may be used.

The Connecting Portion 102 is coated with Connecting Coating 106 which, because of the physical deformations that are applied to this region, will need to be highly flexible. Such a coating would typically be any one of a number of flexible polymers containing conductive particles such as carbon black or powdered metal.

Contact End 107 may be coated with Contact Coating 108, which will make electrical contact with other electrical components of the electrotransport device located outside of the reservoir housing. These typically include, but are not limited to the power source and current regulating circuitry. Contact Coating 108 will effectuate efficient electrically conductive contact with electrical contact pads or other points of contact, on a circuit board or other means of electrical communication which would contain one or more components such as the power source (e.g. batteries), and current regulating circuitry.

Figure 3:
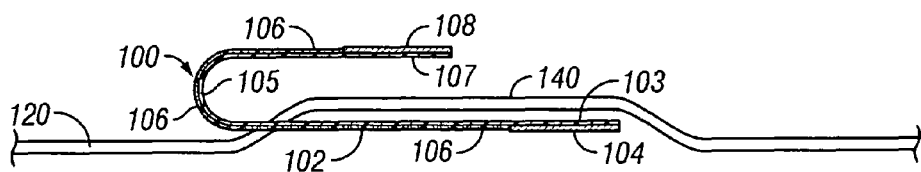
FIG. 3 is a sectional view of a specific implementation of the invention.
Figure 4:
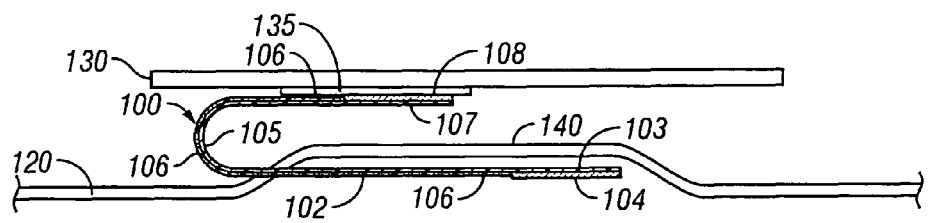
FIG. 4 is a sectional view of an embodiment similar to that shown in FIG. 3, but which also includes a circuit board.

As shown in FIGS. 3 and 4, Reservoir Housing 120 is molded around the Connecting Portion 102 of Flexible Conductor 100. Electrode End 103 is positioned within the reservoir cavity with the Electrode Coating 104 facing towards the open end of the Reservoir Housing 120. Electrode Coating 104 would therefore be in contact with the agent-containing reservoir (not shown) that would be placed within Reservoir Housing 120.

A sufficient length of the Connecting Portion 102 is located outside of the Reservoir Housing 120 so that Flexible Conductor 100 can be bent or folded back on itself and be positioned along the upper Outer Surface 140 of Reservoir Housing 120. Part of the Connecting Portion 102 is located outside of the Reservoir Housing 120 and is called the Flexible Region 105. Because of the significant physical deformation required of Flexible Region 105, Connecting Coating 106 must be sufficiently flexible so that proper electrical conductivity can be maintained while being flexed and yet stay physically attached to Connecting Portion 102, even during significant bending and flexing.

After Connection Portion 102 has been deformed and Flexible Conductor 100 has been bent back on itself, Contact End 107 is now positioned with Contact Coating 108 facing away from Reservoir Housing 120. Typically, Contact Coating 108 is placed in electrical communication with an electrical Contact Pad 135 located on Circuit Board 130, as shown in FIG. 4. However, Contact Coating 108 may be placed in contact with any of a number of standard electrical connections means well known in the industry.

Though Contact End 107 and Circuit Board 130 are shown positioned above Reservoir Housing 120 in FIGS. 3 and 4, the use of Flexible Conductor 100 allows the placement of the Contact End 107 and Contact Coating 108 in any reasonable location relative to Reservoir Housing 120.

Though the embodiment shown describes an underlying flexible substrate with various coatings on top of the substrate, the scope of the invention does not require the use of separate coating layers and includes embodiments in which one or more of the various regions of Flexible Conductor 100: Electrode End 103, Contact End 107 and Connecting Portion 102 are made of a single layer of material which fulfills the required function for each region of the Flexible Conductor 100.

It is further within the scope of the invention that Flexible Conductor 100 can be an integral component formed from a single type of conductive, flexible material.

The above-described exemplary embodiments are intended to be illustrative in all respects, rather than restrictive, of the present invention. Thus, the present invention is capable of implementation in many variations and modifications that can be derived from the description herein by a person skilled in the art. All such variations and modifications are considered to be within the scope and spirit of the present invention.

REFERENCE NUMBER LIST

100 Flexible Conductor
102 Connecting Portion
103 Electrode End
104 Electrode Coating
105 Flexible Region
106 Connecting Coating
107 Contact End
108 Contact Coating
120 Reservoir Housing
130 Circuit Board
135 Contact pad
140 Outer Surface

What is claimed is:

1. An electrotransport device comprising:
a reservoir and a non-conductive housing for the reservoir that comprises a substantially flexible electrically conductive element integrally molded within the non-conductive housing,
the electrically conductive element comprising
an electrode end positioned within the non-conductive housing and coated with an electrode coating;
a connecting portion coated with a connecting coating comprising a flexible polymer; and
a contact end positioned outside the non-conductive housing and coated with a contact coating;
wherein a substantially liquid and moisture-impermeable bond is created between the material forming the non-conductive housing and the conductive element.

2. The electrotransport device of claim 1, wherein the non-conductive housing is a single integral component.

3. The electrotransport device of claim 2, wherein the electrotransport device is manufactured without the fabrication of openings or other passages through the non-conductive housing.

4. The electrotransport device of claim 1, wherein the conductive element comprises a substantially planar member.

5. The electrotransport device of claim 1, wherein the conductive element includes a base member having a conductive coating disposed thereon.

6. The electrotransport device of claim 1, wherein the connection coating contains conductive particles.

* * * * *